United States Patent
Wayama et al.

(10) Patent No.: US 10,653,372 B2
(45) Date of Patent: May 19, 2020

(54) RADIATION IMAGING SYSTEM

(71) Applicant: CANON KABUSHIKI KAISHA, Tokyo (JP)

(72) Inventors: Hiroshi Wayama, Kawasaki (JP); Minoru Watanabe, Yokohama (JP); Keigo Yokoyama, Kawasaki (JP); Satoru Sawada, Kawasaki (JP); Kazuya Furumoto, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 439 days.

(21) Appl. No.: 15/631,205

(22) Filed: Jun. 23, 2017

(65) Prior Publication Data
US 2018/0008215 A1 Jan. 11, 2018

(30) Foreign Application Priority Data
Jul. 8, 2016 (JP) ................................. 2016-136294

(51) Int. Cl.
*A61B 6/00* (2006.01)
*G01T 1/16* (2006.01)

(52) U.S. Cl.
CPC .......... *A61B 6/4208* (2013.01); *A61B 6/4233* (2013.01); *A61B 6/465* (2013.01); *A61B 6/5211* (2013.01); *A61B 6/54* (2013.01); *G01T 1/16* (2013.01)

(58) Field of Classification Search
CPC ..... A61B 6/4208; A61B 6/4233; A61B 6/465; A61B 6/5211; A61B 6/54; G01T 1/16
See application file for complete search history.

(56) References Cited

U.S. PATENT DOCUMENTS

| | | | |
|---|---|---|---|
| 7,205,568 B2 | 4/2007 | Watanabe et al. | 257/59 |
| 7,386,089 B2 | 6/2008 | Endo et al. | 378/5 |
| 7,388,184 B2 | 6/2008 | Izumi et al. | |
| 7,408,167 B2 | 8/2008 | Kameshima et al. | 250/370.09 |
| 7,470,908 B2 | 12/2008 | Ishii et al. | 250/370.08 |
| 7,488,948 B2 | 2/2009 | Ishii et al. | 250/370.11 |
| 7,696,484 B2 | 4/2010 | Yokoyama et al. | 250/370.09 |
| 7,718,973 B2 | 5/2010 | Endo et al. | 250/370.08 |

(Continued)

FOREIGN PATENT DOCUMENTS

| | | |
|---|---|---|
| CN | 101930985 | 12/2010 |
| CN | 102315236 | 1/2012 |

(Continued)

*Primary Examiner* — Michael T Rozanski
(74) *Attorney, Agent, or Firm* — Venable LLP

(57) ABSTRACT

A radiation imaging system includes pixel array, scanning circuit to scan rows of the pixel array, and readout circuit to read signals from the pixel array. Each pixel includes converter to generate electric signal corresponding to radiation and transistor connected to the converter. The readout circuit reads signal from the converter via the transistor. The system performs image capturing modes and conditioning mode of conditioning a threshold voltage of the transistor. In the conditioning mode, the scanning circuit supplies, to a gate of the transistor, an OFF voltage different from OFF voltages in the image capturing modes. The scanning circuit scans the rows in units of at least one row in the image capturing modes, and scans the rows in units of at least two rows in the conditioning mode.

19 Claims, 12 Drawing Sheets

(56) References Cited

U.S. PATENT DOCUMENTS

| | | |
|---|---|---|
| 7,732,776 B2 | 6/2010 | Takenaka et al. ............ 250/369 |
| 7,839,977 B2 | 11/2010 | Kameshima et al. ........ 378/116 |
| 7,897,930 B2 | 3/2011 | Mochizuki et al. ..... 250/370.09 |
| 8,424,764 B2 | 4/2013 | Tanaka et al. |
| 8,530,989 B2 | 9/2013 | Kikuchi et al. |
| 8,687,246 B2 | 1/2014 | Fujimura et al. |
| 2005/0270590 A1* | 12/2005 | Izumi ................ H01L 27/14676 |
| | | 358/474 |
| 2011/0317054 A1 | 12/2011 | Kameshima et al. ........ 348/302 |
| 2015/0316661 A1 | 11/2015 | Fujiyoshi et al. .... G01T 1/2018 |

FOREIGN PATENT DOCUMENTS

| | | |
|---|---|---|
| CN | 102316281 | 1/2012 |
| JP | 2004-147102 A | 5/2004 |
| JP | 2011-101693 A | 5/2011 |
| JP | 2011-216723 A | 10/2011 |
| TW | 200409352 | 6/2004 |
| WO | 2004/039059 | 5/2004 |

\* cited by examiner

IMAGE CAPTURING MODE

CONDITIONING MODE

FIG. 10

IMAGE CAPTURING MODE

| Mode No. | T1[usec] | FRAME RATE [FPS] | BINNING COUNT | T4[ms] | T5[ms] | DUTY RATIO (T1/T4) [%] |
|---|---|---|---|---|---|---|
| 1 | 5 | 30 | 3 | 7.5 | 33.3 | 0.067 |
| 2 | 5 | 30 | 2 | 11.3 | 33.3 | 0.44 |
| 3 | 5 | 30 | 1 | 22.5 | 33.3 | 0.023 |
| 4 | 5 | 30 | 1 | 15.0 | 33.3 | 0.033 |
| 5 | 10 | 30 | 3 | 15.0 | 33.3 | 0.067 |
| 6 | 10 | 30 | 2 | 22.5 | 33.3 | 0.44 |
| 7 | 10 | 30 | 1 | 45.0 | 33.3 | 0.023 |
| 8 | 10 | 30 | 1 | 30.0 | 33.3 | 0.033 |

FIG. 11

CONDITIONING MODE

| Mode No. | T6[usec] | FRAME RATE [FPS] | BINNING COUNT | T9[ms] | T10[ms] | DUTY RATIO (T6/T9) [%] |
|---|---|---|---|---|---|---|
| 11 | 5 | 30 | 3 | 7.5 | 33.3 | 0.067 |
| 12 | 5 | 60 | 3 | 5.0 | 16.7 | 0.100 |
| 13 | 5 | 30 | 4 | 5.6 | 33.3 | 0.089 |
| 14 | 5 | 30 | 6 | 3.8 | 33.3 | 0.133 |
| 15 | 10 | 30 | 3 | 15.0 | 33.3 | 0.067 |
| 16 | 10 | 60 | 3 | 15.0 | 16.7 | 0.067 |
| 17 | 10 | 30 | 4 | 11.3 | 33.3 | 0.089 |
| 18 | 10 | 30 | 6 | 7.5 | 33.3 | 0.133 |

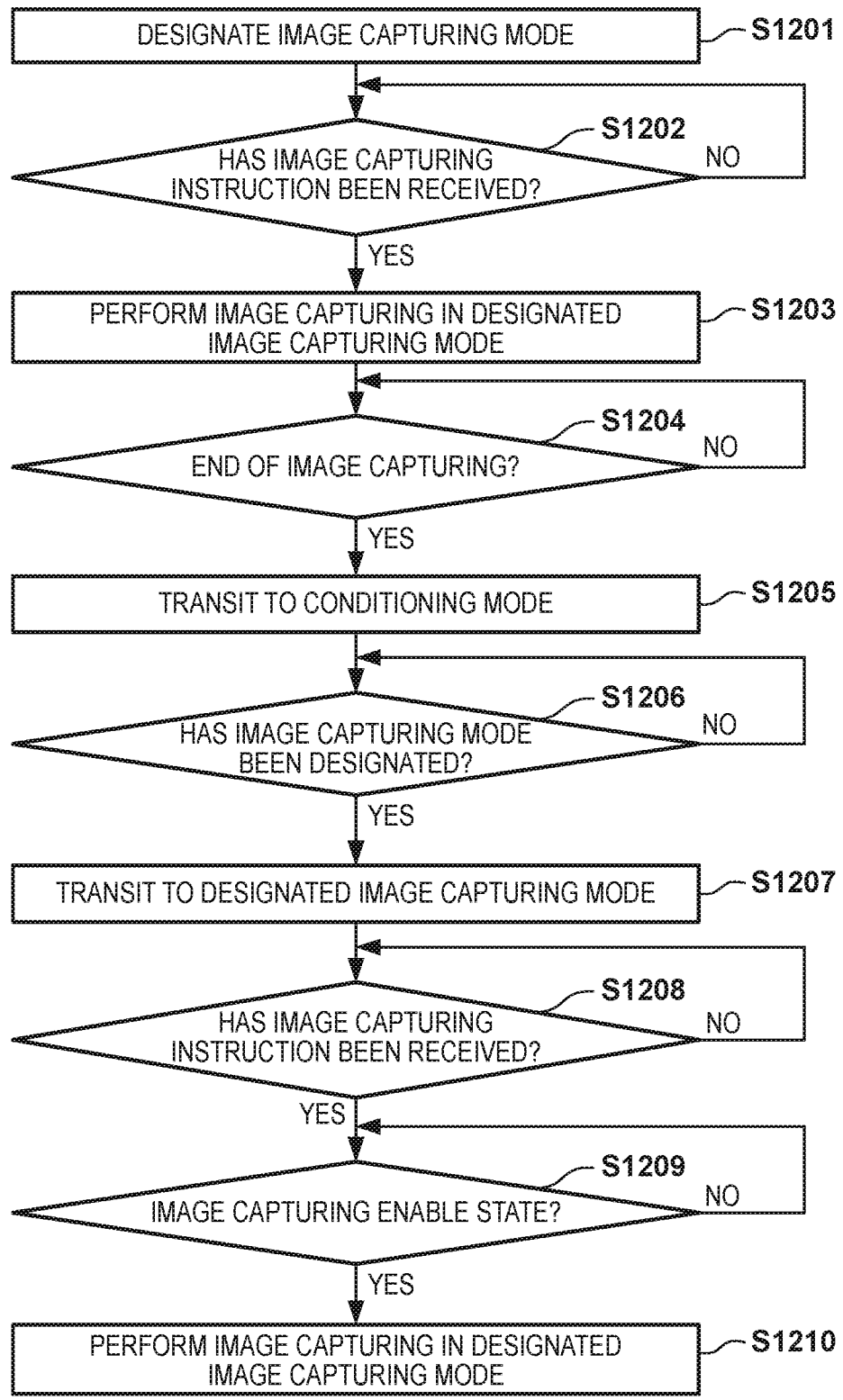

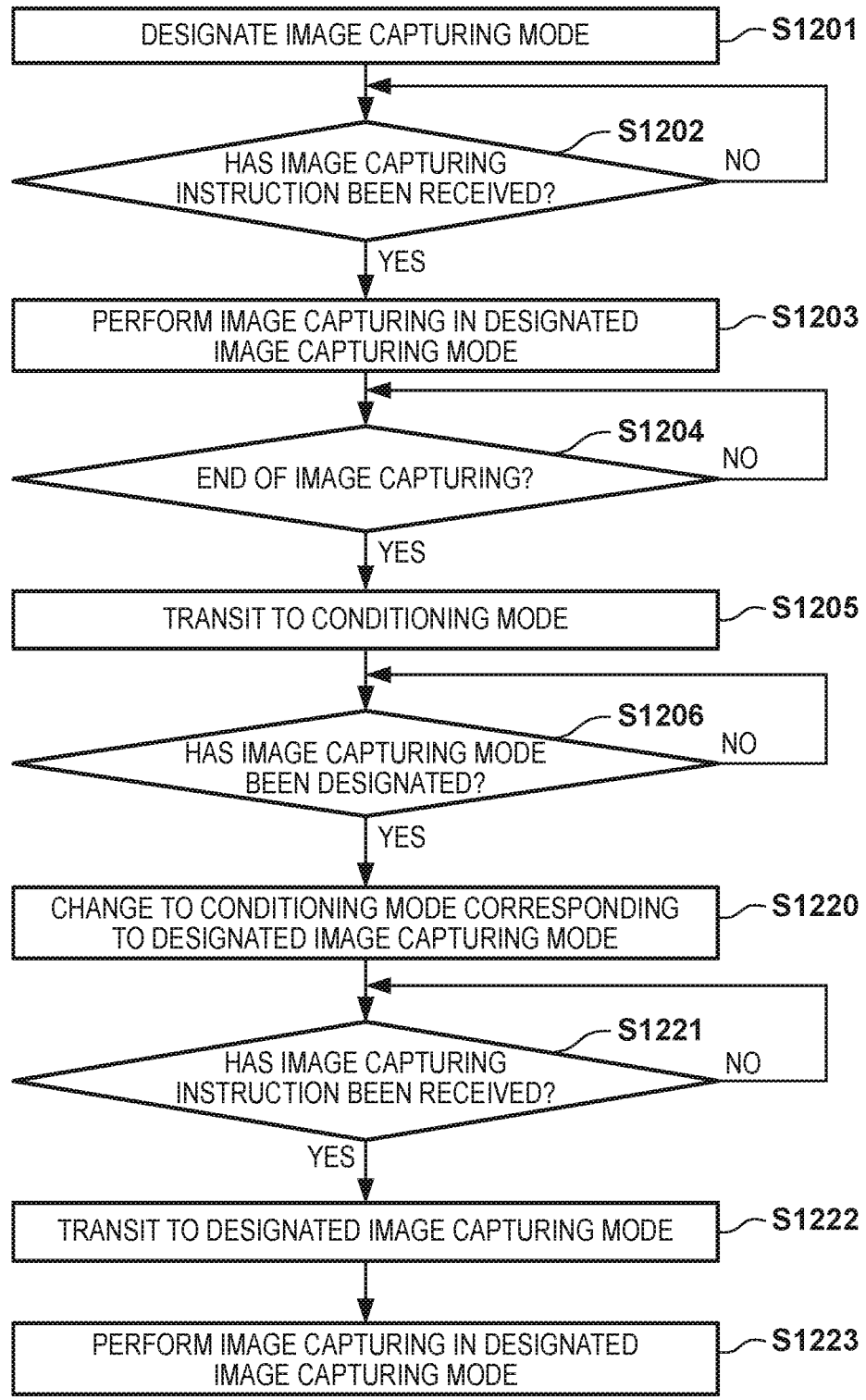

RADIATION IMAGING SYSTEM

BACKGROUND OF THE INVENTION

Field of the Invention

The present invention relates to a radiation imaging system.

Description of the Related Art

A radiation imaging apparatus includes a panel in which a plurality of pixels for detecting radiation are arranged, and a readout circuit for reading out signals from the panel. Each pixel can include a converter for converting radiation into an electric signal, and a transistor connected to the converter. If the radiation imaging apparatus is irradiated with radiation through a subject, signals corresponding to the emitted radiation are accumulated in the converters, and the readout circuit reads out, via the transistor, signals corresponding to the accumulated signals. This obtains a radiation image. In a state in which the radiation imaging apparatus is not irradiated with radiation, noise components can be accumulated in the converters. An image corresponding to the noise components can be read out as an offset image.

The radiation imaging apparatus can obtain an image from which the noise components are removed, by calculating the difference between the radiation image obtained by detecting the irradiated radiation and the offset image obtained in the state in which the radiation imaging apparatus is not irradiated with radiation. However, if the state of the radiation imaging apparatus when obtaining the radiation image is different from the state of the radiation imaging apparatus when obtaining the offset image, it is impossible to correctly remove the noise components from the radiation image. Japanese Patent Laid-Open No. 2011-101693 describes a radiation image forming apparatus which has an imaging enable state and a sleep state, and causes a readout IC to perform a readout operation by supplying power to the readout IC in the sleep state or when transiting from the sleep state to the imaging enable state.

As described above, each pixel of the radiation imaging apparatus includes the converter and the transistor connected to the converter. If an OFF voltage (a voltage for turning off the transistor) is applied to the gate of the transistor of the pixel for a long time, a threshold may shift. If the threshold of the transistor of each pixel shifts, the influence of the shift appears in a radiation image as fixed pattern noise.

SUMMARY OF THE INVENTION

The present invention provides a technique advantageous in improving the image quality by reducing a shift of the threshold of each pixel of a radiation imaging apparatus.

The first aspect of the present invention provides a radiation imaging system including a pixel array having a plurality of pixels which are arranged to form a plurality of rows and a plurality of columns, a scanning circuit configured to scan the plurality of rows of the pixel array, and a readout circuit configured to read out signals from the pixel array, wherein each pixel includes a converter configured to generate an electric signal corresponding to radiation and a transistor connected to the converter, and the readout circuit is configured to read out a signal from the converter of each pixel via the transistor, the radiation imaging system performs a plurality of image capturing modes of capturing a radiation image and a conditioning mode of conditioning a threshold voltage of the transistor of each pixel, and in the conditioning mode, the scanning circuit supplies, to a gate of the transistor, an OFF voltage different from OFF voltages in the plurality of image capturing modes, and the scanning circuit scans the plurality of rows in units of at least one row in the plurality of image capturing modes, and scans the plurality of rows in units of at least two rows in the conditioning mode.

The second aspect of the present invention provides a radiation imaging system including a pixel array having a plurality of pixels which are arranged to form a plurality of rows and a plurality of columns, a scanning circuit configured to scan the plurality of rows of the pixel array, and a readout circuit configured to read out signals from the pixel array, wherein each pixel includes a converter configured to generate an electric signal corresponding to radiation and a transistor connected to the converter, and the readout circuit is configured to read out a signal from the converter of each pixel via the transistor, the radiation imaging system performs a plurality of image capturing modes of capturing a radiation image and a conditioning mode of conditioning a threshold voltage of the transistor of each pixel, and in the conditioning mode, the scanning circuit supplies, to a gate of the transistor, an OFF voltage different from OFF voltages in the plurality of image capturing modes, and when a ratio of an ON period of the transistor of each pixel to a scanning period required to scan the plurality of rows by the scanning circuit is set as a duty ratio, a duty ratio in the conditioning mode is not lower than a lowest value of duty ratios in the plurality of image capturing modes.

Further features of the present invention will become apparent from the following description of exemplary embodiments with reference to the attached drawings.

BRIEF DESCRIPTION OF THE DRAWINGS

FIG. 10 is a table exemplifying a plurality of image capturing modes;

FIG. 11 is a table exemplifying a plurality of conditioning modes;

FIG. 12 is a flowchart illustrating another example of the operation of the radiation imaging system; and FIG. 13 is a flowchart illustrating still another example of the operation of the radiation imaging system.

DESCRIPTION OF THE EMBODIMENTS

The present invention will be described below using an exemplary embodiment of the present invention with reference to the accompanying drawings.

Figure 1:
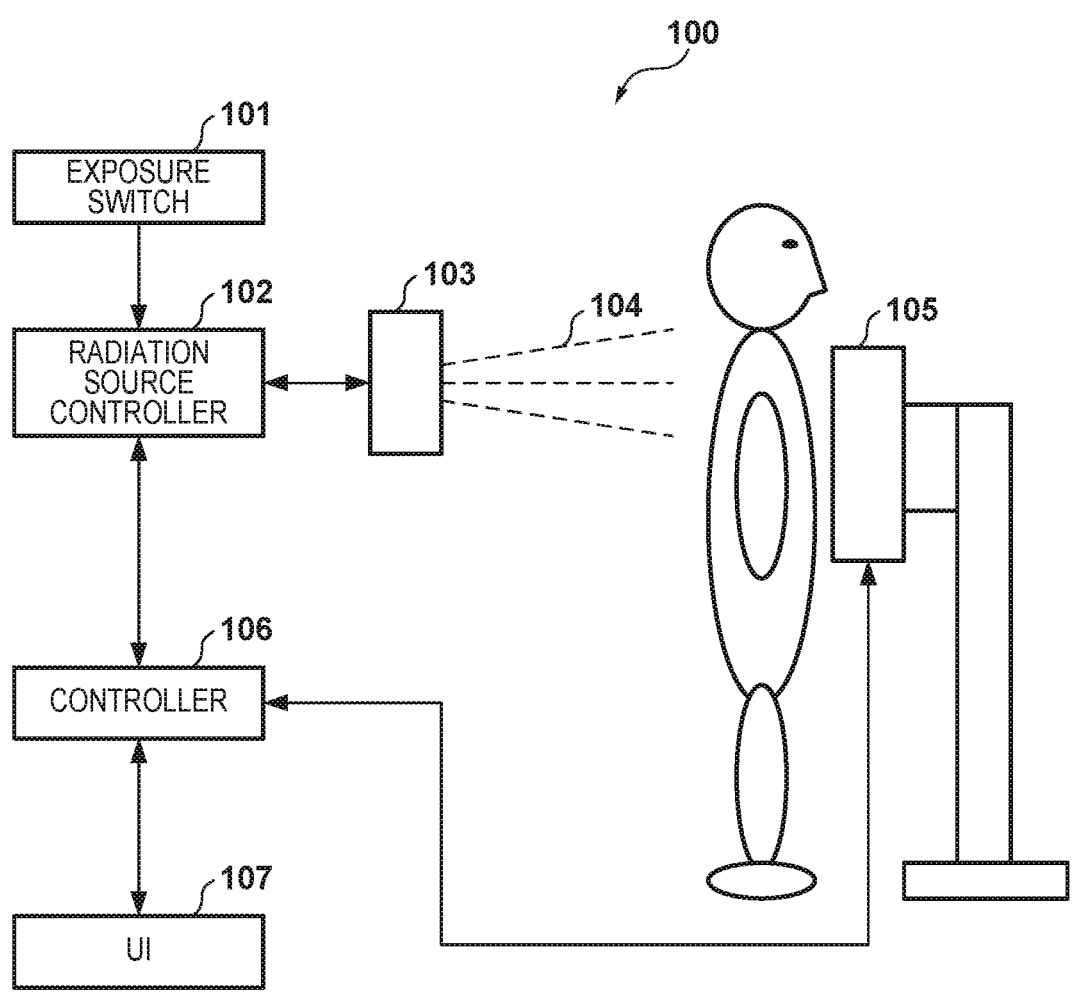
FIG. 1 is a view showing an example of the configuration of a radiation imaging system according to an embodiment of the present invention.

FIG. 1 shows an example of the configuration of a radiation imaging system 100 according to an embodiment of the present invention. The radiation imaging system 100 includes a radiation imager 105. The radiation imaging system 100 can also include an exposure switch 101, a radiation source controller 102, a radiation source 103, a controller 106, and a user interface 107. Some or all of the radiation imager 105, the exposure switch 101, the radiation source controller 102, and the controller 106 may be integrally formed.

The exposure switch 101 is connected to the radiation source controller 102 via a wire or wirelessly, and controls irradiation with radiation 104 from the radiation source 103. When a user such as a doctor or radiographer turns on the exposure switch 101, the radiation source controller 102 causes the radiation source 103 to emit the radiation. A subject is irradiated with the radiation from the radiation source 103. The radiation source controller 102 is connected to the exposure switch 101, the radiation source 103, and the controller 106. The radiation source controller 102 sends a radiation exposure instruction to the radiation source 103 in accordance with a signal provided from the exposure switch 101. The radiation source 103 emits the radiation in accordance with the exposure instruction. The user interface 107 can be formed by, for example, a computer, and include an input device such as a keyboard and pointing device and an output device such as a display. The radiation imager 105 performs, as a plurality of operation modes, a plurality of image capturing modes and at least one conditioning mode (preferably, a plurality of conditioning modes), and the user can select one of the plurality of operation modes via the user interface 107. The controller 106 is connected to the user interface 107, the radiation source controller 102, and the radiation imager 105, and displays a radiation image on the display of the user interface 107 based on information (radiation image) provided from the radiation imager 105.

Figure 2:
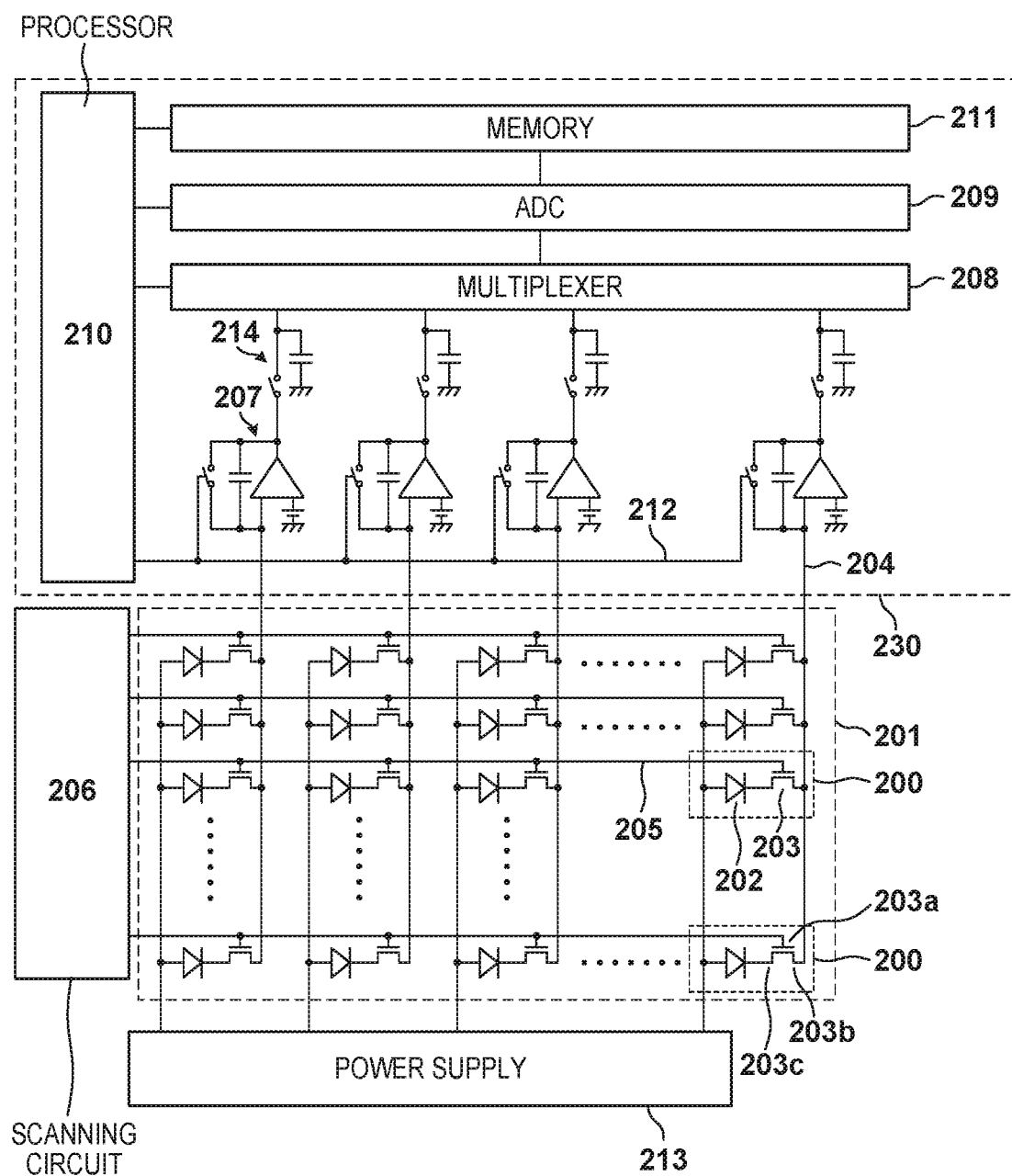
FIG. 2 is a circuit diagram showing an example of the arrangement of a radiation imager.
Figure 3:
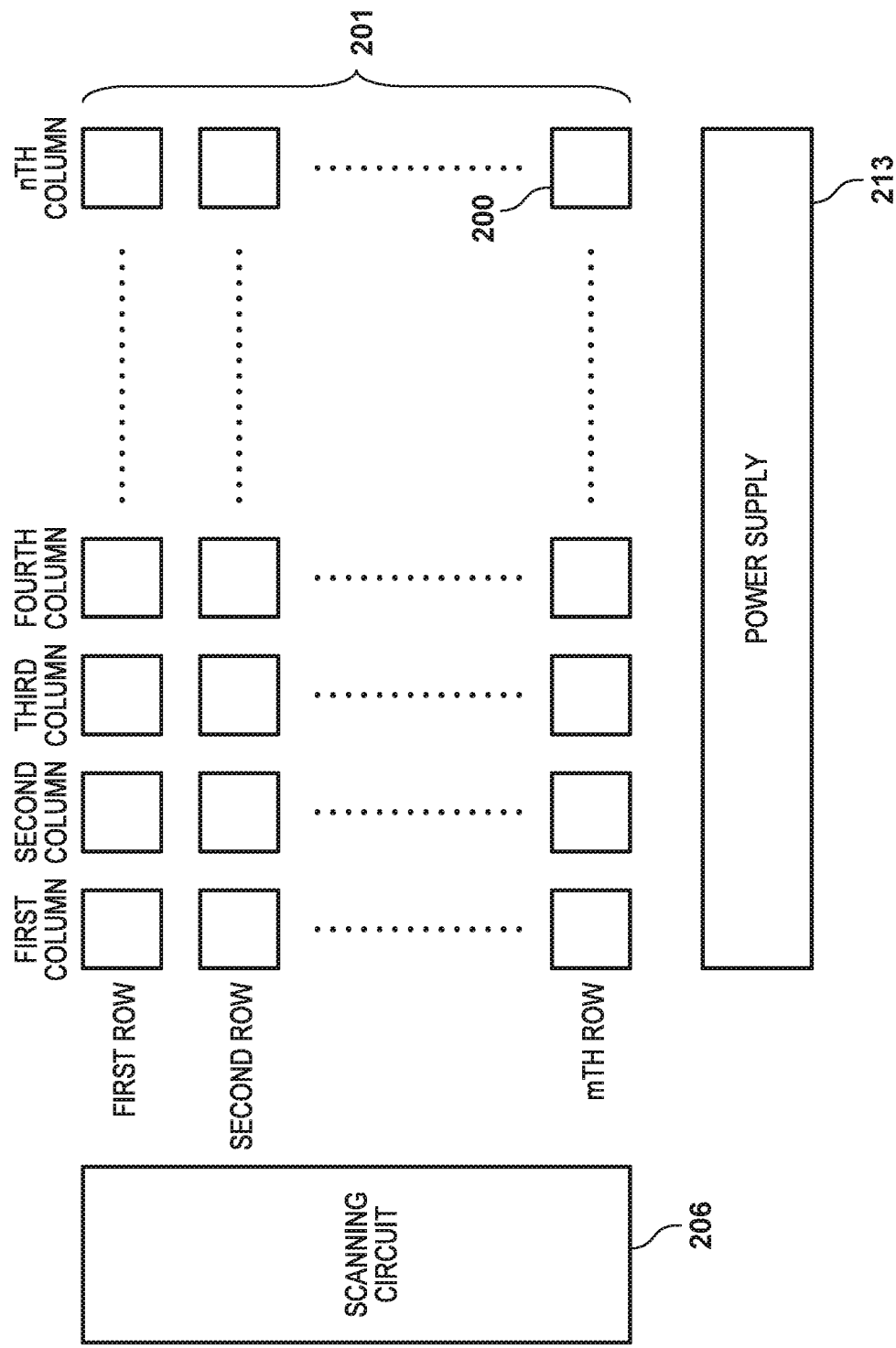
FIG. 3 is a view showing an example of the arrangement of a pixel array.

FIG. 2 shows an example of the arrangement of the radiation imager 105. The radiation imager 105 can include a pixel array 201, a scanning circuit (driving circuit) 206, a readout circuit 230, and a power supply 213. The pixel array 201 includes a plurality of pixels 200 which are arranged to form a plurality (m) of rows and a plurality (n) of columns, as shown in FIGS. 2 and 3. Each pixel 200 includes a converter 202 for generating an electric signal corresponding to radiation, and a transistor 203 connected to the converter 202. The converter 202 can include, for example, a scintillator for converting the radiation into visible light, and a photoelectric converter for converting the visible light into an electric signal. This arrangement is called an indirect type, in which the scintillator converts radiation into visible light, and the photoelectric converter photoelectrically converts the visible light. The scintillator can be shared by the plurality of pixels 200. In the indirect type, amorphous silicon or polysilicon can be shared as a semiconductor. The scintillator can be made of, for example, gadolinium oxysulfide (GOS) or cesium iodide (CsI). The converter 202 may be formed by an element for directly converting the radiation into an electric signal. This arrangement is called a direct type. In the direct type, amorphous selenium can be adopted as a semiconductor.

The transistor 203 can form a switch for connecting a signal line 204 connected to the readout circuit 230 and the converter 202 of the pixel 200. Alternatively, the pixel 200 may include an in-pixel readout circuit, and the transistor 203 may form a switch for connecting the converter 202 and the in-pixel readout circuit. The transistor 203 can be formed by, for example, a thin-film transistor. The transistor 203 includes a gate 203a, a source 203b, and a drain 203c. In an example, the drain 203c is connected to the converter 202, and the source 203b is connected to the signal line 204.

The scanning circuit 206 drives the pixels 200 on the plurality of rows of the pixel array 201 in units of at least one row. The scanning circuit 206 drives a plurality of driving lines 205 respectively corresponding to the plurality of rows of the pixel array 201. The driving line 205 of each row is connected to the gates 203a of the transistors 203 of the pixels 200 on the row. Each row of the pixel array 201 is selected by supplying, to the driving line 205 of the row, a voltage for turning on the transistors 203 connected to the driving line 205. The scanning circuit 206 selects the pixels 200 on the plurality of rows of the pixel array 201 in units of at least one row in a set order. This operation is called a scan.

Figure 4:
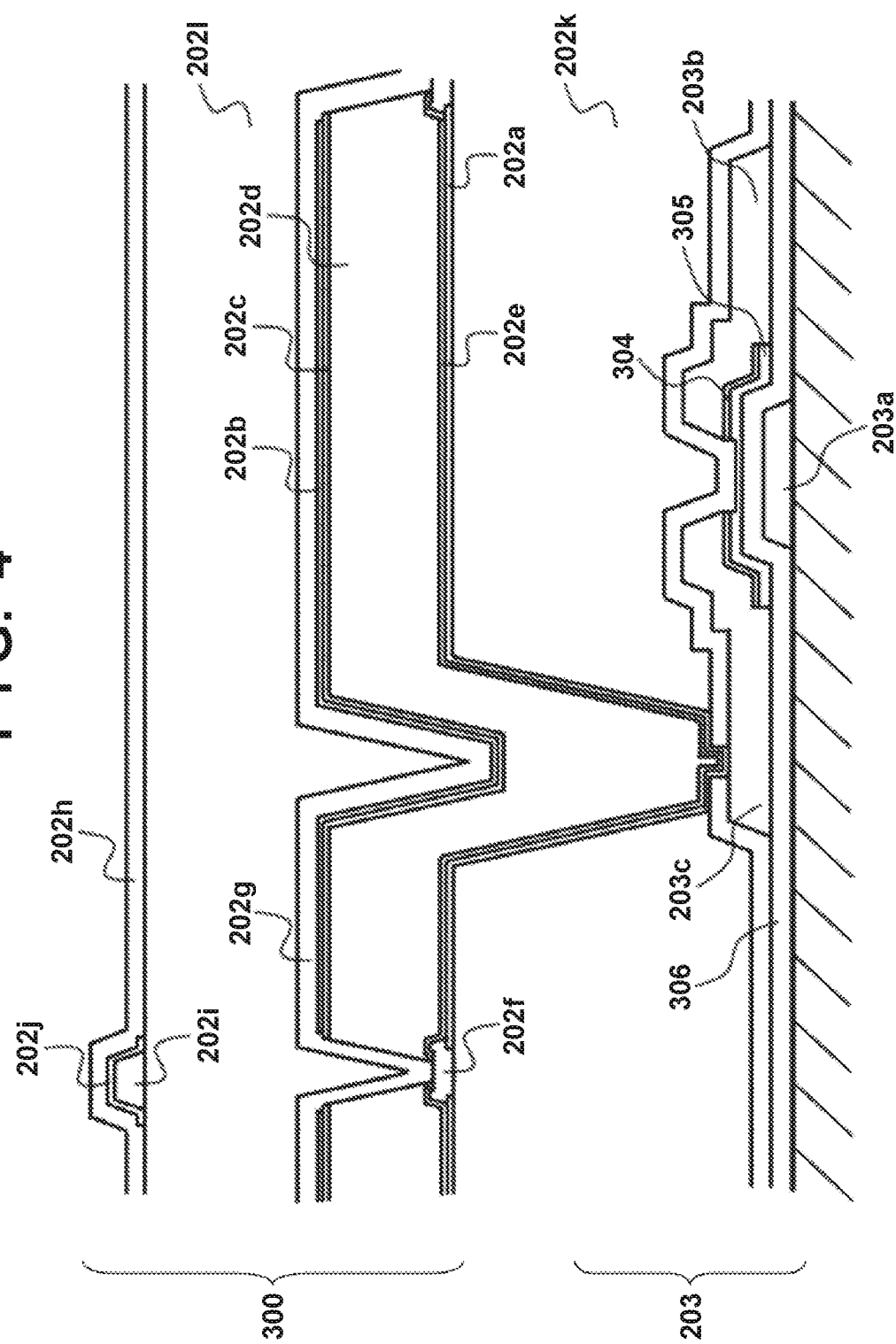
FIG. 4 is a view exemplifying the structure of a pixel formed by a PIN-type converter and a thin-film transistor.

FIG. 4 exemplifies the pixel 200 in which the converter 202 is formed by a PIN-type converter 300 and the transistor 203 is formed by a thin-film transistor. The PIN-type converter 300 includes, from above, a p-type semiconductor 202c, an intrinsic semiconductor 202d, an n-type semiconductor 202e. A common electrode 202b is arranged on the p-type semiconductor 202c and a discrete electrode 202a is arranged under the n-type semiconductor 202e. The p-type semiconductor 202c, the intrinsic semiconductor 202d, and the n-type semiconductor 202e are separated for each pixel, and a first insulating layer 202f exists between the pixels. A second insulating layer 202g and a second planarization film 202l are arranged on the common electrode 202b, and a metal layer 202i and a transparent electrode layer 202j exit on the second planarization film 202l. Although not shown, the metal layer 202i and the transparent electrode layer 202j are connected to the common electrode 202b.

The thin-film transistor serving as the transistor 203 includes the gate 203a, the source 203b, and the drain 203c. The drain 203c is connected to the discrete electrode 202a of the converter 202. A first planarization film 202k is arranged between the transistor 203 and the PIN-type converter 300 serving as the converter 202.

Figure 5:
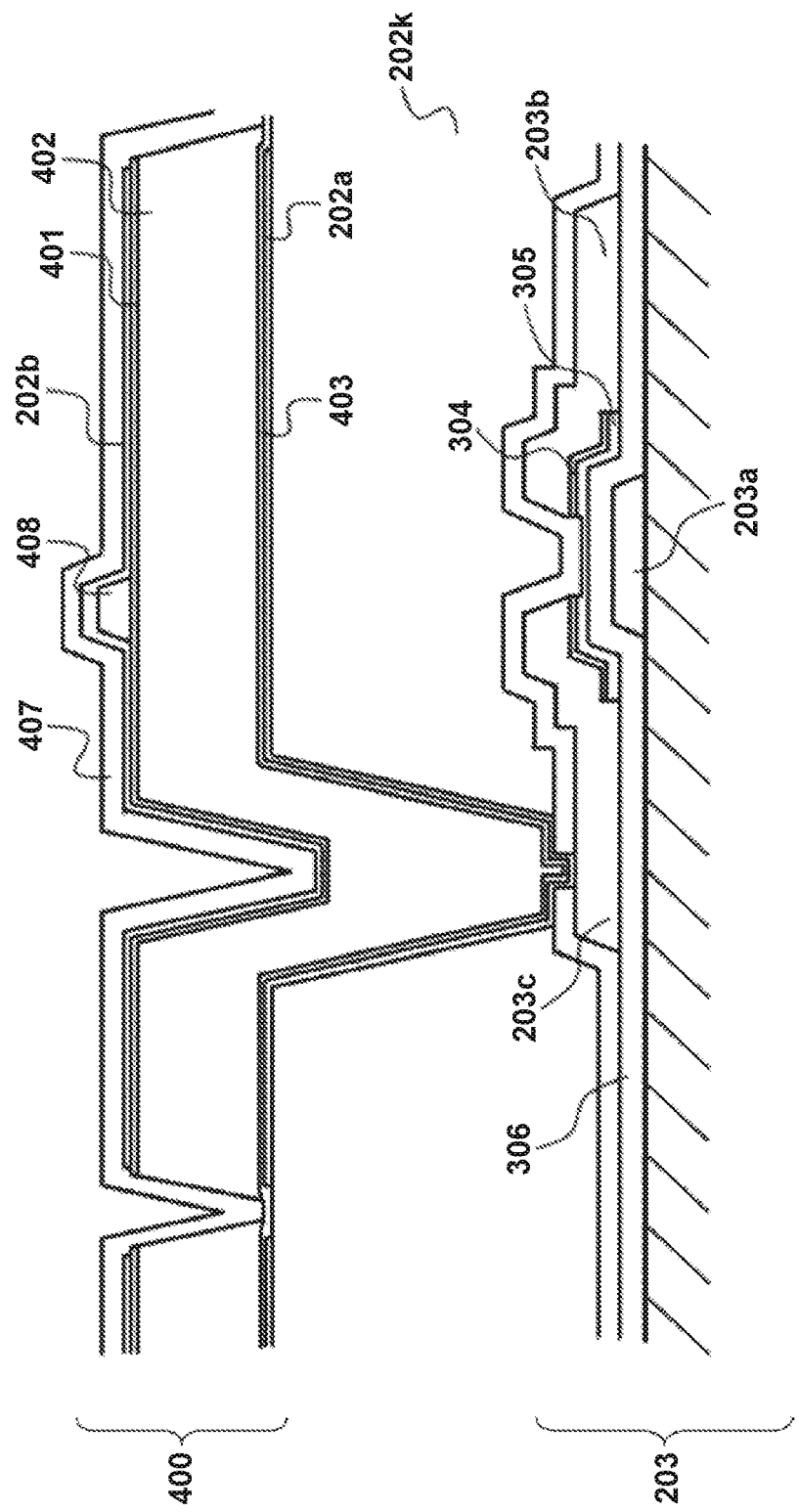
FIG. 5 is a view exemplifying the structure of a pixel formed by a MIS-type converter and a thin-film transistor.

FIG. 5 exemplifies the pixel 200 in which the converter 202 is formed by a MIS-type converter 400 and the transistor 203 is formed by a thin-film transistor. The MIS-type converter 400 includes, from above, an n-type semiconductor 401, an intrinsic semiconductor 402, and a first insulating layer 403. The common electrode 202b is arranged on the n-type semiconductor 401, and the discrete electrode 202a is arranged under the first insulating layer 403.

The common electrode 202b of the converter 202 (PIN-type converter 300 or MIS-type converter 400) is connected to the power supply 213, and has a potential fixed by the power supply 213. The discrete electrode 202a of the converter 202 is connected to the transistor 203. An electric field is generated in the converter 202 (PIN-type converter 300 or MIS-type converter 400). In the indirect type, visible light enters the converter 202, thereby generating a pair of an electron and a hole by photoelectric conversion. One of the electron and hole is attracted to the common electrode 202b which has the potential fixed by the power supply 213. The other is accumulated in the converter 202, and the potential of the discrete electrode 202a varies. If, for example, the transistor 203 is formed by an n-type thin-film transistor and the converter 202 is formed by the MIS-type converter 400, the transistor 203 and the discrete electrode 202a are connected and the potential of the discrete electrode 202a varies due to the incidence of light.

The thin-film transistor serving as the transistor 203 includes a semiconductor layer 305 and an insulating layer 306 in addition to the gate 203a, the source 203b, and the drain 203c. If the semiconductor layer 305 is an n-type semiconductor layer, an n-type transistor is formed. If the semiconductor layer 305 is a p-type semiconductor layer, a p-type transistor is formed. As for the n-type transistor, when the voltage of the gate 203a becomes higher than a threshold voltage, the transistor is set in an ON state. As for the p-type transistor, when the voltage of the gate 203a becomes lower than the threshold voltage, the transistor is set in the ON state. The gate 203a is connected to the driving line 205, the source 203b is connected to the signal line 204, and the drain 203c is connected to the discrete electrode 202a of the converter 202. Furthermore, as the structure of the thin-film transistor 203, a bottom gate type thin-film transistor having the driving line 205 located below the transistor 203 or a top gate type thin-film transistor having the driving line 205 located above the transistor 203 may be adopted.

The converter 202 and the transistor 203 are generally formed by using a CVD (Chemical Vapor Deposition) apparatus. Some or all of the components of the converter 202 and the transistor 203 may be formed by the same film forming process or all of the components may be formed by different film forming processes. The arrangement examples shown in FIGS. 4 and 5 are formed by the latter method. When the scanning circuit 206 supplies a voltage for turning on the transistor 203 to its gate 203a, the transistor 203 is turned on. This supplies, to an amplification circuit 207 of the readout circuit 230 via the signal line 204, a signal corresponding to charges accumulated in the converter 202.

Figure 6:
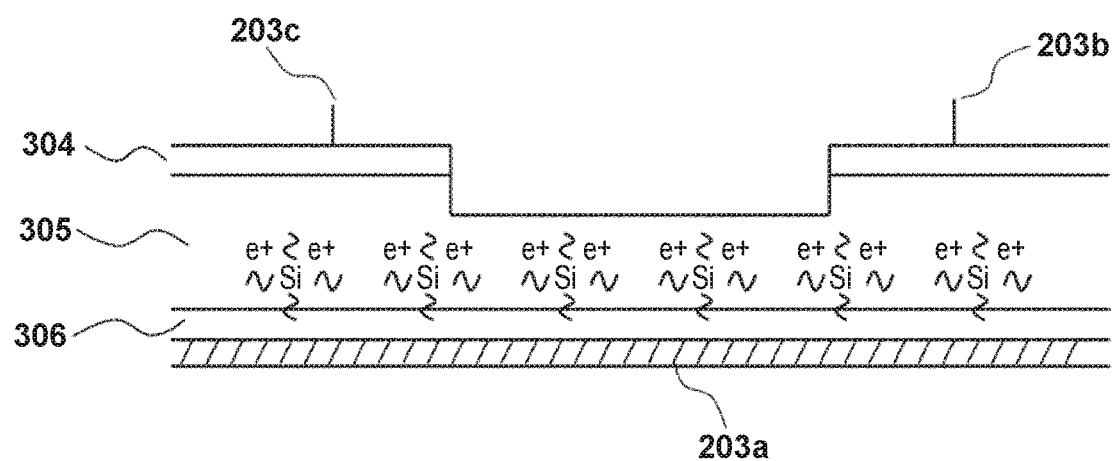
FIG. 6 is a view for explaining a change in threshold voltage of the transistor.

The transistor 203 includes the insulating layer 306, and the semiconductor layer 305 in which charges move, and has a channel formed in the semiconductor layer 305. In the n-type transistor, if a negative voltage is applied to the gate 203a for a long time, holes (e+) are trapped (accumulated) at the boundary between the insulating layer 306 and the semiconductor layer 305, as schematically shown in FIG. 6. The trapped holes shift the threshold of the transistor 203 to the minus side. If an OFF voltage applied to the gate 203a of the transistor 203 changes, the trapped holes are released from a trapped state to generate a dark current, thereby finally influencing an image. The OFF voltage is a voltage for turning off the transistor 203. The number of holes which are released from the trapped state decreases with the lapse of certain time, and becomes 0 after all. After changing the OFF voltage to be applied to the gate 203a, therefore, it is desirable to capture a radiation image after standing by until the behavior of the holes released from the trapped state is relaxed sufficiently. In the p-type transistor, it is desirable to capture a radiation image after standing by until electrons are trapped and the behavior of the electrons is settled down.

If the transistor 203 is formed by the n-type thin-film transistor, the scanning circuit 206 applies a negative voltage of, for example, about −15 to −5 V to the gate 203a as an OFF voltage, and applies a positive voltage of, for example, about 5 to 20 V to the gate 203a as an ON voltage. If the transistor 203 is formed by the p-type thin-film transistor, the scanning circuit 206 applies a positive voltage of, for example, about 5 to 20 V to the gate 203a as an OFF voltage, and applies a negative voltage of, for example, about −15 to −5 V to the gate 203a as an ON voltage. The ON voltage is a voltage for turning on the transistor 203.

The scanning circuit 206 scans the plurality of rows of the pixel array 201 in units of at least one row. Therefore, during most of a period in which the radiation imager 105 operates, an OFF voltage is generally applied to the gate 203a of the transistor 203 of each pixel 200. If, therefore, the transistor 203 is the n-type transistor, when a negative voltage is dominantly applied to the gate, the threshold shifts in the negative direction. Conversely, if the transistor 203 is the p-type transistor, when a positive voltage is dominantly applied to the gate, the threshold shifts in the positive direction. The progress of such shift is faster in the n-type transistor as the OFF voltage is stronger in the negative direction, and is faster in the p-type transistor as the OFF voltage is stronger in the positive direction. Thus, by making the OFF voltage close to the ground potential, it is possible to suppress the shift of the threshold.

The readout circuit 230 can include, for example, the amplification circuit 207, a multiplexer 208, a sample/hold circuit 214, an ADC (analog-to-digital converter) 209, a memory 211, and a processor 210. The processor 210 can be configured to control the amplification circuit 207, the multiplexer 208, the ADC 209, and the memory 211. The amplification circuit 207 amplifies signals output from the pixel array 201 via the plurality of signal lines 204. The signals amplified by the amplification circuit 207 are sampled and held by the sample/hold circuit 214. The amplification circuit 207 includes a plurality of column amplification circuits respectively corresponding to the plurality of columns (the plurality of signal lines 204) of the pixel array 201. Each column amplification circuit is reset by a reset signal supplied from the processor 210 via a reset signal line 212. The multiplexer 208 sequentially selects the signals output in parallel from the sample/hold circuit 214, and outputs them to the ADC 209, which converts the signals into digital data. The memory 211 temporarily holds the digital data output from the ADC 209, and supplies them to the processor 210.

The operation of the radiation imager 105 or the radiation imaging system 100 will be described below. Note that a case in which the transistor 203 is formed by the n-type thin-film transistor will be described as an example. The OFF voltage of the transistor 203 is a negative voltage, and the ON voltage of the transistor 203 is a positive voltage. As an example, the OFF voltage of the transistor 203 is a voltage within the range of −5 V to −20 V, the ON voltage of the transistor 203 is a voltage within the range of 5 V to 20 V, and the threshold voltage of the transistor 203 is a voltage within the range of 0 V to 3 V.

As described above, the radiation imager 105 performs, as the plurality of operation modes, the plurality of image capturing modes and at least one conditioning mode (preferably, the plurality of conditioning modes). The image capturing mode is a mode of capturing a radiation image, and the conditioning mode is a mode of conditioning the threshold voltage of the transistor 203 of each pixel 200 of the pixel array 201. In the conditioning mode, the scanning circuit 206 supplies, to the gate of the transistor 203 of the pixel 200, an OFF voltage different from the OFF voltages in the plurality of image capturing modes. In the plurality of image capturing modes, the scanning circuit 206 scans the plurality of rows of the pixel array 201 in units of at least one row. In the conditioning mode, the scanning circuit 206 scans the plurality of rows of the pixel array 201 in units of at least two rows.

Figure 7:
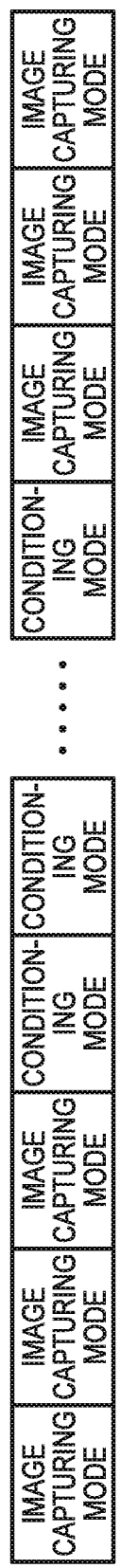
FIG. 7 is a view showing an example of the operation of the radiation imaging system.

FIG. 7 exemplifies a sequence of performing an image capturing operation in the image capturing mode a plurality of times, performing a conditioning operation in the conditioning mode a plurality of times, and then performing the image capturing operation in the image capturing mode a plurality of times. Each box in FIG. 7 indicates a unit operation in the repetitive operation, and the unit operation includes at least an operation in which the scanning circuit 206 scans the plurality of rows (all the rows) of the pixel array 201 once. A radiation image of one frame is captured by the unit operation in the image capturing mode. The unit operation in the image capturing mode includes an accumulation operation and a readout operation. The period of the unit operation in the image capturing mode can include an accumulation period during which the accumulation operation is performed and a readout period during which the readout operation is performed. The accumulation operation is an operation in which the plurality of pixels 200 of the pixel array 201 accumulate electric signals corresponding to the radiation. In the accumulation operation, the scanning circuit 206 supplies an OFF voltage to the gates of all the transistors 203 of the plurality of pixels 200 of the pixel array 201. The readout operation is an operation in which the readout circuit 230 reads out the signals while the scanning circuit 206 scans the plurality of pixels 200 of the pixel array 201 in units of at least one row. The scan by the scanning circuit 206 is an operation of sequentially selecting the plurality of rows of the pixel array 201 in units of at least one row. Selection of a row indicates supply of an ON voltage to the gates of the transistors 203 of the pixels 200 on the row. The unit operation in the image capturing mode can include repetition of a reset operation before the accumulation operation. The reset operation is an operation in which the scanning circuit 206 scans the plurality of rows to reset the plurality of pixels 200 of the pixel array 201.

The unit operation in the conditioning mode includes a scanning operation in which the scanning circuit 206 scans the pixels 200 on the plurality of rows (all the rows) of the pixel array 201. The unit operation in the conditioning mode may include a standby operation in addition to the scanning operation. The period of the unit operation in the conditioning mode includes at least a scanning period during which the scanning operation is performed, and can also include a standby period during which the standby operation is performed.

In the image capturing mode of capturing a moving image, the start and end timings of the unit operation are, for example, the start and end timings of an operation for capturing a radiation image of one frame, and can be defined by a synchronization signal for defining the frame. In the image capturing mode of capturing a moving image, the radiation source controller 102 causes the radiation source 103 to emit the radiation in accordance with the synchronization signal.

The plurality of operation modes of the radiation imager 105 may further include a calibration mode of acquiring an offset image. In general, the processor 210 generates a corrected radiation image by calculating the difference between a radiation image acquired by the image capturing operation in the image capturing mode and an offset image acquired by an offset image acquisition operation in the calibration mode.

Figure 8:
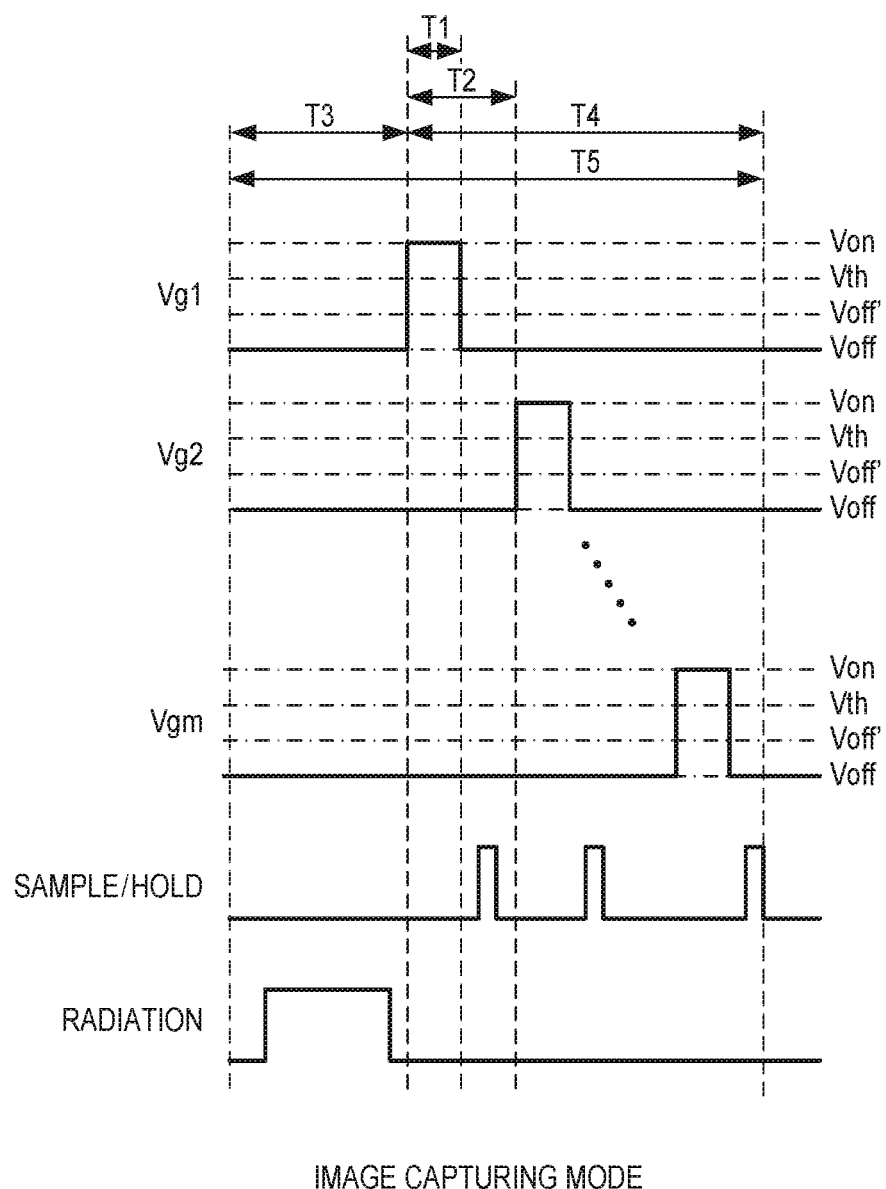
FIG. 8 is a timing chart exemplifying the unit operation of an image capturing operation in an image capturing mode.

FIG. 8 exemplifies the unit operation of the image capturing operation in one image capturing mode. Vg1 to Vgm respectively represent driving signals output from the scanning circuit 206 to the driving lines 205 on the first to mth rows, that is, driving signals supplied to the gates 203a of the transistors 203 of the pixels 200 on the first to mth rows. In other words, Vgi (i=1 to m) represents a driving signal of the ith row. Furthermore, Von represents the ON voltage, Voff represents the OFF voltage, Vth represents the threshold voltage of the transistor 203, and GND represents the ground voltage. Voff' represents the OFF voltage (an OFF voltage for conditioning the threshold voltage) in the conditioning mode, and a voltage between Voff and Von. Note that Vg1 to Vgm, Von, Voff, Vth, GND, and Voff' are also used in other drawings.

T1 represents a period during which the driving signal of each row is set at the ON voltage Von in the image capturing mode. In other words, T1 represents a period (ON period), during which the transistor 203 of each pixel 200 is turned on, in the scanning period required to scan, by the scanning circuit 206, the plurality of rows of the pixel array 201 in the image capturing mode. T2 represents a period from when the driving signal of a given row is set at the ON voltage Von until the driving signal of a row to be supplied with the ON voltage next is set at the ON voltage Von in the capturing mode. T3 represents an accumulation period. T4 represents a readout period, and also a scanning period in the image capturing mode. In other words, T4 represents a period required to amplify (read out), by the amplification circuit 207, the signals of the pixels on all rows, to be read out, of the pixel array 201 and to sample the signals by the sample/hold circuit 214. A period during which the "radiation" is at a high level is a period during which the radiation imager 105 is irradiated with the radiation. T5 represents the period of the unit operation, and is given by the sum of the accumulation period T3 and the readout period (scanning period) T4.

In the image capturing mode, the readout circuit 230 reads out the signals of the pixels 200 on the first to mth rows while the scanning circuit 206 scans (sequentially selects) the pixels 200 on the first to mth rows of the pixel array 201 in units of at least one row. The radiation imager 105 can have a plurality of image capturing mode Nos. 01 to 08, as exemplified in FIG. 10. The plurality of image capturing mode Nos. 01 to 08 exemplified in FIG. 10 are image capturing modes of capturing a moving image, and can include, for example, an image capturing mode of performing energy subtraction image capturing or tomosynthesis image capturing in addition to an image capturing mode of performing general moving image capturing. FIG. 10 exemplifies T1, T4, T1/T4, and the like. T1/T4 represents the ratio of the ON period of the transistor 203 of each pixel 200 to the scanning period required to scan, by the scanning circuit 206, the plurality of rows of the pixel array 201 in the image capturing mode. The ratio (T1/T4) is a duty ratio in the image capturing mode. The plurality of image capturing modes can include image capturing modes in which duty ratios are different.

If the user wants to end the series of image capturing operations, he/she instructs the user interface 107 to end image capturing. In response to this, the controller 106 controls the radiation imager 105 to end the image capturing mode to transit to the conditioning mode. Alternatively, the controller 106 may control the radiation imager 105 to transit from the image capturing mode to the conditioning mode by detecting that the user has not performed any operation for a predetermined period.

Figure 9:
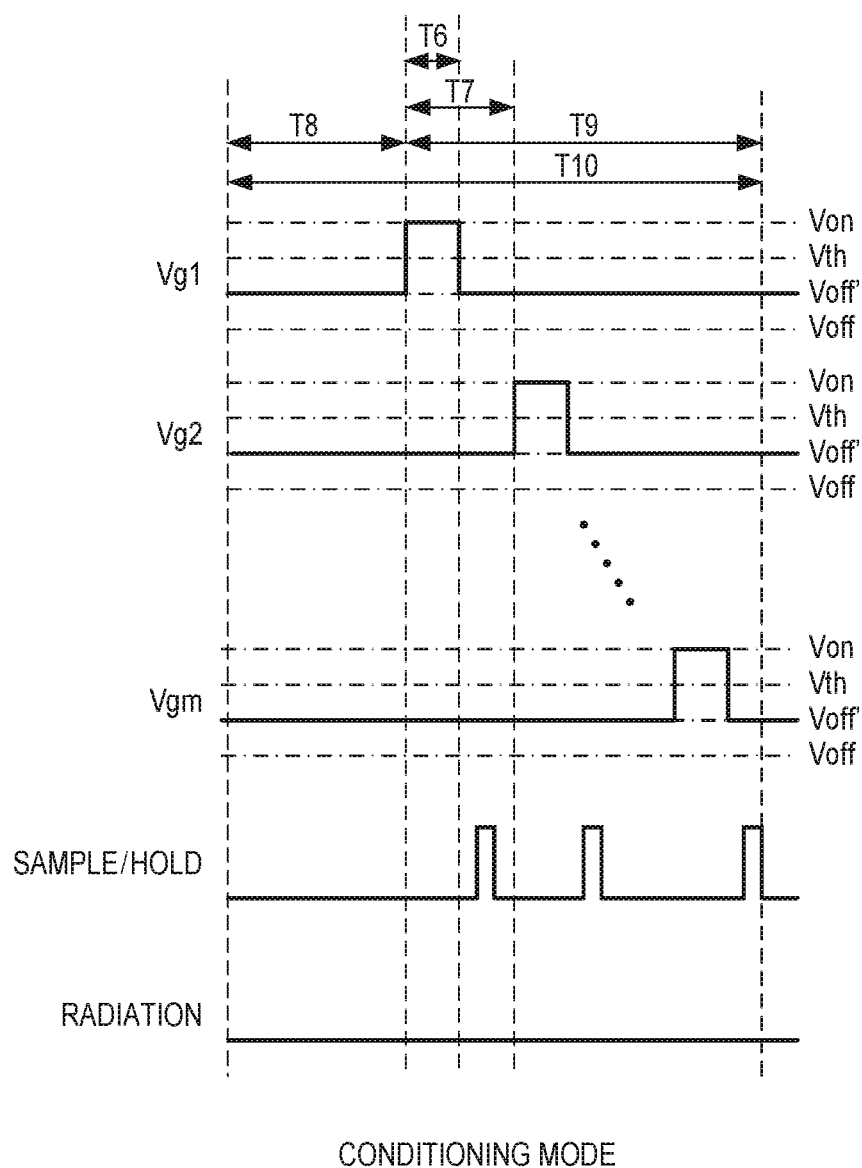
FIG. 9 is a timing chart exemplifying the unit operation of a conditioning operation in a conditioning mode.

FIG. 9 exemplifies the unit operation of the conditioning operation in the conditioning mode. In the conditioning mode, the scanning circuit 206 scans (sequentially selects) the pixels 200 on the first to mth rows of the pixel array 201 in units of at least two rows. More specifically, in the conditioning mode, the scanning circuit 206 sequentially selects the pixels 200 on the first to mth rows of the pixel array 201 in units of at least two rows, and supplies the ON voltage Von to the gates 203a of the transistors 203 of the selected pixels 200. At this time, the readout circuit 230 may read out the signals of the pixels 200 on the rows forming the selected unit. An image formed by the signals can be used as an offset image or a correction image.

The scanning circuit 206 supplies the OFF voltage Voff' for conditioning the threshold voltage to the gates 203a of the transistors 203 of the unselected pixels 200. This weakens a force (electrostatic force) by which holes existing in an intrinsic semiconductor 203d of the transistor 203 are attracted to the gates 203a applied with a negative potential. Thus, the shift of the threshold voltage can be suppressed. In an example, if the OFF voltage Voff is a voltage within the range of −20 V to −10 V, the OFF voltage Voff' for conditioning the threshold can be a voltage within the range of −10 V to 0 V, which satisfies |Voff|>|Voff'|.

As described above, in the conditioning mode, the scanning circuit 206 scans (sequentially selects) the pixels 200 on the first to mth rows of the pixel array 201 in units of at least two rows. This can shorten the time required to perform a scan by the scanning circuit 206, as compared with a case in which the pixels 200 on the first to mth rows of the pixel array 201 are scanned row by row. This means that the duty ratio in the conditioning mode can be increased. By increasing the duty ratio, a time during which the ON voltage Von is supplied to the gates 203a of the transistors 203 of the selected pixels 200 can be prolonged. This is advantageous in suppressing the shift of the threshold voltage of the transistor 203.

T6 represents a period during which the driving signal of each row is set at the ON voltage Von in the conditioning mode. In other words, T6 represents a period (ON period), during which the transistor 203 of each pixel 200 is turned on, in the scanning period required to scan, by the scanning circuit 206, the plurality of rows of the pixel array 201 in the conditioning mode. T7 represents a period from when the driving signal of a given row is set at the ON voltage Von until the driving signal of a row to be supplied with the ON voltage next is set at the ON voltage Von. T8 represents a standby period, and a period during which the scanning circuit 206 supplies the OFF voltage to the gates of all the transistors 203 of the plurality of pixels 200 of the pixel array 201. T9 represents a scanning period required to scan, by the scanning circuit 206, the plurality of rows of the pixel array 201 in the conditioning mode. T10 represents a period during which the unit operation is performed in the conditioning mode. In the example shown in FIG. 9, T10 represents the sum of the standby period T8 and the scanning period T9.

The radiation imager 105 can have a plurality of conditioning mode Nos. 11 to 18, as exemplified in FIG. 11. FIG. 11 exemplifies T6, T9, T6/19, and the like. T6/19 is the ratio of the ON period of the transistor 203 of each pixel 200 to the scanning period required to scan, by the scanning circuit 206, the plurality of rows of the pixel array 201 in the conditioning mode. The ratio (T6/19) is a duty ratio in the conditioning mode. The plurality of conditioning modes can include conditioning modes in which duty ratios are different.

It was confirmed through an experiment that the threshold voltage of the transistor 203 shifted when the duty ratio in the conditioning mode was lower than the lowest value of the duty ratios in the plurality of image capturing modes. It was also confirmed through the experiment that the shift of the threshold voltage of the transistor 203 was sufficiently suppressed when the duty ratio in the conditioning mode was equal to or lower than the lowest value of the duty ratios in the plurality of image capturing modes.

FIG. 12 shows another operation of the radiation imaging system 100. The operation shown in FIG. 12 can be controlled by the controller 106. In step S1201, the controller 106 receives designation of an image capturing mode by the user via the user interface 107. In step S1202, the controller 106 receives an instruction to request the start of image capturing by the user via the user interface 107 or the exposure switch 101, and advances to step S1203. In step S1203, the controller 106 controls the radiation imager 105 to perform image capturing in the image capturing mode designated in step S1201. In step S1204, the controller 106 receives an instruction to request the end of image capturing by the user via the user interface 107 or the exposure switch 101, and advances to step S1205.

In step S1205, the controller 106 transits from the image capturing mode to a conditioning mode associated with the image capturing mode. At this time, the conditioning mode corresponding to the image capturing mode can be selected in accordance with a table indicating a pair of the image capturing mode and its corresponding conditioning mode. In step S1206, the controller 106 stands by until designation of an image capturing mode by the user via the user interface 107 is received during execution of the conditioning mode. Upon receiving designation, the controller 106 advances to step S1207. In step S1207, the controller 106 controls the radiation imager 105 to transit from the conditioning mode to the designated image capturing mode. This causes the radiation imager 105 to repeat, in the designated image capturing mode, a reset operation in which the scanning circuit 206 scans the plurality of rows, so as to reset the plurality of pixels of the pixel array 201.

In step S1208, the controller 106 receives an instruction to request the start of image capturing by the user via the user interface 107 or the exposure switch 101, and advances to step S1209. In step S1209, the controller 106 determines whether the radiation imaging system 100 is in a radiation image capturing enable state. If the image capturing enable state is determined, the controller 106 advances to step S1210. The image capturing enable state indicates, for example, a state in which a time for sufficiently reducing fixed pattern noise (fixed pattern noise caused by a variation in amount of charges accumulated at the boundary between the insulating layer 306 and the semiconductor layer 305) has elapsed after returning from the conditioning mode to the image capturing mode in step S1205. In step S1210, the controller 106 controls the radiation imager 105 to perform image capturing in the image capturing mode to which transition has been performed in step S1207.

FIG. 13 shows still another operation of the radiation imaging system 100. The operation shown in FIG. 13 can be controlled by the controller 106. The operation up to step S1206 shown in FIG. 13 is the same as that shown in FIG. 12. In step S1220, the controller 106 changes from the current conditioning mode to a conditioning mode corresponding to an image capturing mode designated in step S1206. The conditioning mode corresponding to the image capturing mode designated in step S1206 can be selected in accordance with the above-described table.

In step S1221, the controller 106 receives an instruction to request the start of image capturing by the user via the user interface 107 or the exposure switch 101, and advances to step S1222. In step S1222, the controller 106 controls the radiation imager 105 to transit from the conditioning mode to the designated image capturing mode. Next, in step S1223, the controller 106 controls the radiation imager 105 to perform image capturing in the image capturing mode designated in step S1206.

The operation of the controller 106 may be executed by a controller provided in the radiation imager 105.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-136294, filed Jul. 8, 2016, which is hereby incorporated by reference herein in its entirety.

What is claimed is:

1. A radiation imaging system including a pixel array having a plurality of pixels which are arranged to form a plurality of rows and a plurality of columns, a scanning circuit configured to scan the plurality of rows of the pixel array, and a readout circuit configured to read out signals from the pixel array, wherein
    each pixel includes a converter configured to generate an electric signal corresponding to radiation and a transistor connected to the converter, and the readout circuit is configured to read out a signal from the converter of each pixel via the transistor,
    the radiation imaging system performs a plurality of image capturing modes of capturing a radiation image and a conditioning mode of conditioning a threshold voltage of the transistor of each pixel, and in the conditioning mode, the scanning circuit supplies, to a gate of the transistor, an OFF voltage different from OFF voltages in the plurality of image capturing modes, and
    the scanning circuit scans the plurality of rows in units of at least one row in the plurality of image capturing modes, and scans the plurality of rows in units of at least two rows in the conditioning mode.

2. The system according to claim 1, wherein when a ratio of an ON period of the transistor of each pixel to a scanning period required to scan the plurality of rows by the scanning circuit is set as a duty ratio, a duty ratio in the conditioning mode is not lower than a lowest value of duty ratios in the plurality of image capturing modes.

3. The system according to claim 1, the system performing a plurality of conditioning modes including the mode of conditioning the threshold voltage of the transistor of each pixel, and further comprising:
    a controller configured to select a conditioning mode from the plurality of conditioning modes.

4. The system according to claim 3, wherein in response to an end of image capturing in one image capturing mode among the plurality of image capturing modes, the controller transits to a conditioning mode corresponding to the one image capturing mode among the plurality of conditioning modes.

5. The system according to claim 3, wherein in a case where one image capturing mode among the plurality of image capturing modes is designated during execution of one conditioning mode among the plurality of conditioning modes, the controller transits to a conditioning mode corresponding to the one image capturing mode among the plurality of conditioning modes, and then transits to the one image capturing mode in response to a request to instruct start of image capturing.

6. The system according to claim 1, wherein in a case where, among the plurality of image capturing modes, an image capturing mode for capturing the radiation image after an end of the conditioning mode is designated during execution of the conditioning mode, transition from the conditioning mode to the designated image capturing mode is performed,
    in the designated image capturing mode, a reset operation in which the scanning circuit scans the plurality of rows is repeated to reset the plurality of pixels, and
    in response to an instruction to request start of image capturing, the radiation image is captured in the designated image capturing mode.

7. The system according to claim 1, wherein the system performs a plurality of conditioning modes including the mode of conditioning the threshold voltage of the transistor of each pixel,
    in a case where one image capturing mode among the plurality of image capturing modes is designated during execution of one conditioning mode selected from the plurality of conditioning modes, transition from the one conditioning mode to a conditioning mode corresponding to the designated image capturing mode among the plurality of conditioning modes is performed, and
    in response to an instruction to request start of image capturing, image capturing is executed in the designated image capturing mode.

8. The system according to claim 1, wherein in the conditioning mode, a unit operation including an operation of scanning the plurality of rows by the scanning circuit and an operation of turning off all the transistors of the plurality of pixels is repeated.

9. The system according to claim 1, further comprising a radiation source.

10. The system according to claim 1, wherein the converter includes an intrinsic semiconductor arranged between a first electrode and a second electrode, and a semiconductor of a first conductive type arranged between the second electrode and the intrinsic semiconductor,
    the transistor includes the gate, a semiconductor layer of a second conductivity type that is different from the first conductivity type, a source, and a drain connected to the first electrode, and a voltage which is supplied to the gate of the transistor by the scanning circuit in the conditioning mode to turn off the transistor is a voltage between a voltage which is supplied to the gate of the transistor by the scanning circuit in the plurality of image capturing modes to turn on the transistor and a voltage which is supplied to the gate of the transistor by the scanning circuit in the plurality of image capturing modes to turn off the transistor.

11. A radiation imaging system including a pixel array having a plurality of pixels which are arranged to form a plurality of rows and a plurality of columns, a scanning circuit configured to scan the plurality of rows of the pixel array, and a readout circuit configured to read out signals from the pixel array, wherein each pixel includes a converter configured to generate an electric signal corresponding to radiation and a transistor connected to the converter, and the readout circuit is configured to read out a signal from the converter of each pixel via the transistor, the radiation imaging system performs a plurality of image capturing modes of capturing a radiation image and a conditioning mode of conditioning a threshold voltage of the transistor of each pixel, and in the conditioning mode, the scanning circuit supplies, to a gate of the transistor, an OFF voltage different from OFF voltages in the plurality of image capturing modes, and when a ratio of an ON period of the transistor of each pixel to a scanning period required to scan the plurality of rows by the scanning circuit is set as a duty ratio, a duty ratio in the conditioning mode is not lower than a lowest value of duty ratios in the plurality of image capturing modes.

12. The system according to claim 11, the system performing a plurality of conditioning modes including the mode of conditioning the threshold voltage of the transistor of each pixel, and further comprising:

a controller configured to select a conditioning mode from the plurality of conditioning modes.

13. The system according to claim 12, wherein in response to an end of image capturing in one image capturing mode among the plurality of image capturing modes, the controller transits to a conditioning mode corresponding to the one image capturing mode among the plurality of conditioning modes.

14. The system according to claim 12, wherein in a case where one image capturing mode among the plurality of image capturing modes is designated during execution of one conditioning mode among the plurality of conditioning modes, the controller transits to a conditioning mode corresponding to the one image capturing mode among the plurality of conditioning modes, and then transits to the one image capturing mode in response to a request to instruct start of image capturing.

15. The system according to claim 11, wherein in a case where, among the plurality of image capturing modes, an image capturing mode for capturing the radiation image after an end of the conditioning mode is designated during execution of the conditioning mode, transition from the conditioning mode to the designated image capturing mode is performed, in the designated image capturing mode, a reset operation in which the scanning circuit scans the plurality of rows is repeated to reset the plurality of pixels, and in response to an instruction to request start of image capturing, the radiation image is captured in the designated image capturing mode.

16. The system according to claim 11, the system performing a plurality of conditioning modes including the mode of conditioning the threshold voltage of the transistor of each pixel, wherein in a case where one image capturing mode among the plurality of image capturing modes is designated during execution of one conditioning mode selected from the plurality of conditioning modes, transition from the one conditioning mode to a conditioning mode corresponding to the designated image capturing mode among the plurality of conditioning modes is performed, and in response to an instruction to request start of image capturing, image capturing is executed in the designated image capturing mode.

17. The system according to claim 11, wherein in the conditioning mode, a unit operation including an operation of scanning the plurality of rows by the scanning circuit and an operation of turning off all the transistors of the plurality of pixels is repeated.

18. The system according to claim 11, further comprising a radiation source.

19. The system according to claim 11, wherein the converter includes an intrinsic semiconductor arranged between a first electrode and a second electrode, and a semiconductor of a first conductive type arranged between the second electrode and the intrinsic semiconductor, the transistor includes the gate, a semiconductor of a second conductivity type that is different from the first conductivity type, a source, and a drain connected to the first electrode, and a voltage which is supplied to the gate of the transistor by the scanning circuit in the conditioning mode to turn off the transistor is a voltage between a voltage which is supplied to the gate of the transistor by the scanning circuit in the plurality of image capturing modes to turn on the transistor and a voltage which is supplied to the gate of the transistor by the scanning circuit in the plurality of image capturing modes to turn off the transistor.

* * * * *